United States Patent
Pellegrino et al.

(10) Patent No.: US 6,981,948 B2
(45) Date of Patent: Jan. 3, 2006

(54) BONE MARROW ASPIRATION SYSTEM

(75) Inventors: Richard C. Pellegrino, Mendon, MA (US); John C. Voellmicke, Cumberland, RI (US)

(73) Assignee: DePuy Spine, Inc., Raynham, MA (US)

( * ) Notice: Subject to any disclaimer, the term of this patent is extended or adjusted under 35 U.S.C. 154(b) by 371 days.

(21) Appl. No.: 10/298,371

(22) Filed: Nov. 18, 2002

(65) Prior Publication Data

US 2004/0097828 A1   May 20, 2004

(51) Int. Cl.
*A61B 10/00*   (2006.01)
(52) U.S. Cl. ...................................... 600/562
(58) Field of Classification Search ................ 600/562, 600/566, 567; 604/272
See application file for complete search history.

(56) References Cited

U.S. PATENT DOCUMENTS

| | | | |
|---|---|---|---|
| 4,366,822 A * | 1/1983 | Altshuler | 600/566 |
| 4,381,006 A | 4/1983 | Genese | |
| 4,393,879 A | 7/1983 | Milgrom | |
| 4,755,172 A | 7/1988 | Baldwin | |
| 4,863,429 A | 9/1989 | Baldwin | |
| 5,108,381 A * | 4/1992 | Kolozsi | 604/319 |
| 5,197,485 A * | 3/1993 | Grooters | 600/571 |
| 5,575,293 A * | 11/1996 | Miller et al. | 600/565 |
| 5,824,084 A | 10/1998 | Muschler | |
| 6,049,026 A | 4/2000 | Muschler | |
| 6,135,320 A | 10/2000 | Parsons | |
| 6,406,454 B1 | 6/2002 | Hajianpour | |
| 6,736,799 B1 * | 5/2004 | Erbe et al. | 604/181 |
| 6,796,957 B2 * | 9/2004 | Carpenter et al. | 604/93.01 |
| 2002/0045903 A1 | 4/2002 | Bonutti | |
| 2002/0127720 A1 | 9/2002 | Erbe et al. | |
| 2002/0161449 A1 | 10/2002 | Muschler | |
| 2003/0130594 A1 * | 7/2003 | Hynes et al. | 600/562 |

FOREIGN PATENT DOCUMENTS

| | | |
|---|---|---|
| EP | 0 931 519 A1 | 7/1999 |
| WO | WO 02/40963 A2 | 5/2002 |
| WO | WO 03/006099 A1 | 1/2003 |
| WO | WO 03/057046 A2 | 7/2003 |

* cited by examiner

*Primary Examiner*—Max F. Hindenburg
*Assistant Examiner*—Brian Szmal
(74) *Attorney, Agent, or Firm*—Nutter, McClennen & Fish LLP

(57) ABSTRACT

Bone marrow aspiration devices and methods are disclosed for use in preparing a substrate. In general, the device includes an elongate penetrating element, a chamber adapted to retain a substrate, and a fluid extraction mechanism that is effective to pull fluid through the elongate penetrating element, into the chamber, and through the substrate. The device is particularly advantageous in that it will allow for the removal of fluids from a patient's body and the preparation of a substrate in a single process, thereby providing a more efficient method and device for preparing a substrate.

33 Claims, 4 Drawing Sheets

BONE MARROW ASPIRATION SYSTEM

FIELD OF THE INVENTION

The present invention relates to devices and methods for preparing a substrate, and in particular to bone marrow aspiration devices and methods for preparing implantable bone grafts.

BACKGROUND OF THE INVENTION

Bone grafts are often used to treat fractures, gaps in bones caused by trauma or infection, revision joint surgery, and oral/maxillofacial surgery. Bone grafts provide a framework into which the host bone can regenerate and heal. Once implanted, the bone cells weave into and through the porous microstructure of the bone graft to support the new tissue, blood cells and soft tissue as they grow to connect fractured bone segments.

Bone grafts can be prepared from a variety of materials, including bone harvested from a patient. Bone harvesting procedures, however, can result in significant cost and morbidity, including scars, blood loss, pain, prolonged operative and rehabilitation time and risk of infection. Furthermore, in some clinical settings, the volume of the graft site can exceed the volume of the available autograft. Accordingly, alternative graft materials have been developed in an attempt to reduce the morbidity and cost of bone grafting procedures. Such alternative materials include purified or synthetic materials, such as ceramics, biopolymers, processed allograft bone and collagen-based matrices. These materials are typically used as carriers for bone marrow cells, and thus need to be prepared prior to implantation.

Current procedures typically involve a two-step process which includes the withdrawal of bone marrow from a patient into several syringes, and then the subsequent preparation of the bone graft. The bone graft can be prepared by flushing the aspirated bone marrow one or more times to collect and concentrate the stem cells contained in the marrow into the bone graft. While this procedure can be very effective, it can also be time consuming typically requiring around 20 minutes for the aspiration procedure, and an additional 20 minutes for the graft preparation procedure.

Accordingly, there is a need for more efficient methods and devices for preparing substrates.

SUMMARY OF THE INVENTION

In general, the present invention provides a bone marrow aspiration device having a chamber adapted to retain a substrate, an elongate penetrating element extending from a distal end of the chamber and having a proximal end, a distal end, and an inner lumen extending therebetween, and a fluid extraction mechanism coupled to the proximal end of the chamber and effective to draw fluid into the elongate penetrating element, and through a substrate disposed in the chamber. The device can also include a fluid permeable tray or container removably disposed within the chamber for retaining a substrate.

In one embodiment, the chamber is an elongate, cylindrical barrel, and the fluid extraction mechanism is a plunger disposed within the barrel and having a handle adapted to move the plunger proximally to extract fluid through the device. The chamber is preferably adapted to retain a substrate in a position proximal to an inlet port formed in the distal end of the chamber. In another embodiment, the device includes a control member mated to the fluid extraction mechanism and effective to control the amount of fluid being extracted by the fluid extraction mechanism. The control member is preferably effective to control the rate of fluid being extracted by the fluid extraction mechanism. The control member can be, for example, a trigger mechanism effective to actuate the fluid extraction mechanism to extract a predetermined amount of fluid.

In another embodiment, the device includes a fluid receptacle in communication with the chamber. The fluid receptacle is adapted to receive fluid passed through the chamber and through a substrate disposed within the chamber. The substrate is preferably disposed at an inlet port of the fluid receptacle, and the fluid receptacle is preferably removably mated to the chamber. The device can optionally include a unidirectional valve disposed between the chamber and the fluid receptacle for allowing fluid to flow only in a direction from the chamber to the fluid receptacle. The unidirectional valve can be disposed at the proximal end of the chamber such that fluid can flow from the chamber through the unidirectional valve, then through a substrate, and into the fluid receptacle.

In other aspects, the device includes a conduit extending between the proximal end of the elongate penetrating element and the inlet port of the chamber such that fluid can flow from the elongate penetrating element, through the conduit, and into the chamber. The conduit can be removably attached to the proximal end of the elongate penetrating element and the inlet port in the chamber. The device can also include a second conduit extending from the outlet port of the chamber to an inlet port in the fluid receptacle for allowing fluid to flow from the chamber to the receptacle, and a third conduit extending from the outlet port of the fluid receptacle to the fluid extraction mechanism.

The present invention also provides methods for preparing a substrate. The method generally includes the step of providing a bone marrow aspirator device having an elongate penetrating element having a proximal end, a distal end adapted to penetrate bone, and an inner lumen extending therebetween. A chamber is in fluid communication with the proximal end of the elongate penetrating element, and a substrate is disposed within the chamber. The penetrating element also includes a fluid extraction mechanism effective to pull fluid through the elongate penetrating element, into the chamber, and through the substrate. The method further includes the steps of penetrating the distal end of the elongate penetrating element into a patient, and actuating the fluid extraction mechanism to pull fluid from the patient through the elongate penetrating element, into the chamber, and through the substrate, thereby concentrating cells from a biological material within the substrate.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides bone marrow aspiration devices and methods for preparing a substrate by extracting fluids directly from a patient through a substrate. In general, the device includes an elongate penetrating element, a chamber adapted to retain a substrate, and a fluid extraction mechanism that is effective to pull fluid through the elongate penetrating element, into the chamber, and through the substrate. The device is particularly advantageous in that it will allow for the removal of fluids from a patient's body and the preparation of a substrate in a single process, thereby providing a more efficient method and device for preparing a substrate.

A person having ordinary skill in the art will appreciate that a variety of substrates and fluids can be used with the system of the present invention, and that the term "substrate" as used herein is intended to encompass both implantable and non-implantable substrates, used alone or in combination with other substrates. By way of non-limiting example, suitable implantable substrates include bone grafts, fusion cages, ceramic bone substitutes, soft tissue grafts, such as skin tendons, and ligaments, and other suitable implantable material, and suitable non-implantable substrates include filters for filtering particular elements from a fluid. In an exemplary embodiment, the present invention is used to prepare an implantable substrate by flowing fluid therethrough, and one or more filters are optionally used in combination with the implantable substrate. The filter(s) can be positioned upstream and/or downstream from the implantable substrate, and can be adapted to filter particular elements from a fluid, such as, for example, red blood cells from plasma. Alternatively, or in addition, the filter can contain a biological agent or fluid for treating fluid passing therethrough. Suitable fluids for use with the present invention include, for example, fluids having regenerative properties, such as bone marrow, blood, platelet rich plasma, placenta, synovial fluid, and amniotic fluid, and suspensions containing stem cells, growth factors, and proteins.

Figure 1:
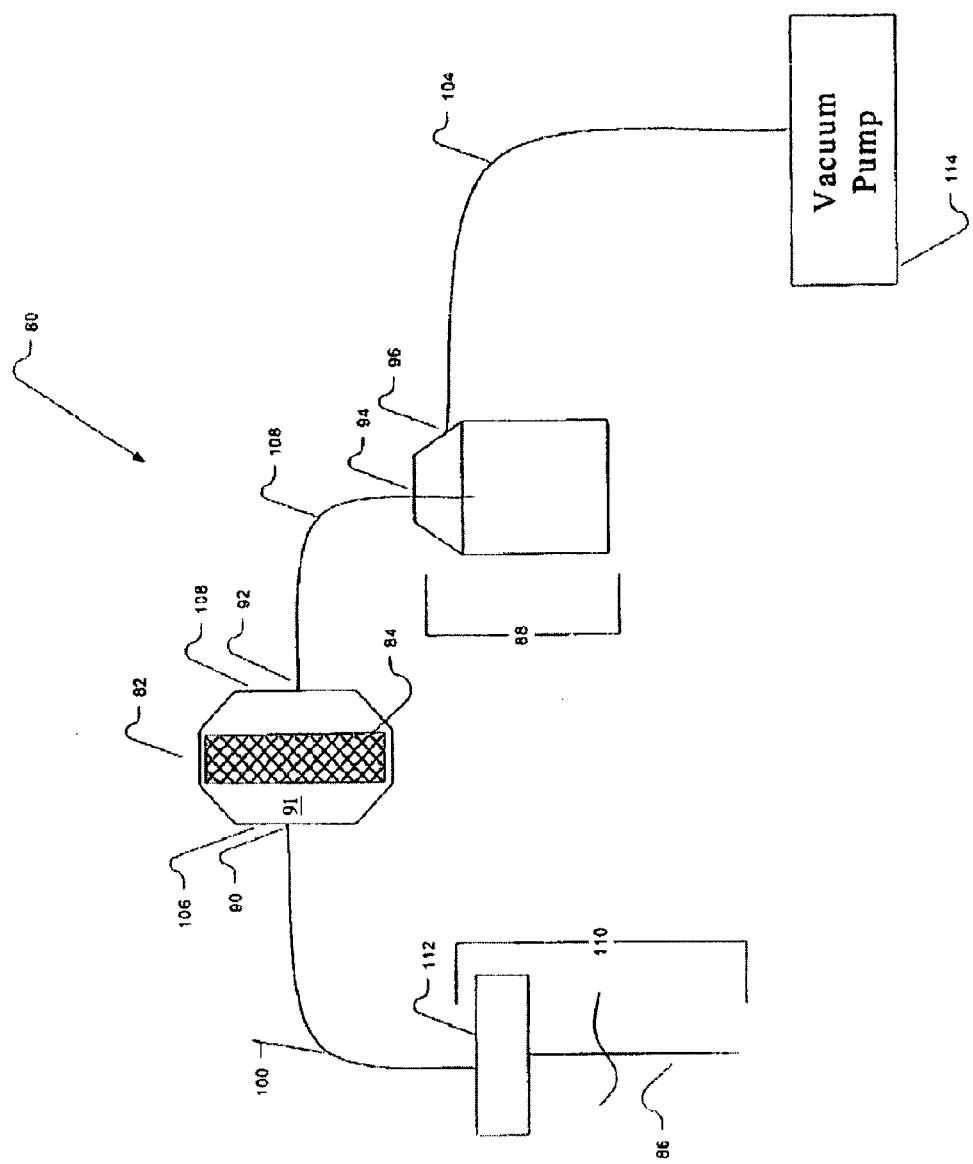
FIG. 1 is a diagram illustrating one embodiment of a bone marrow aspiration device having an elongate penetrating element, a chamber, a fluid receptacle, and a fluid extraction mechanism.

FIG. 1 illustrates one embodiment of a bone marrow aspiration device 80 according to the present invention. As shown, the device 80 includes a chamber 82 that is adapted to retain at least one substrate 84, a penetrating element 110 coupled to an inlet 90 formed in the chamber 82, and a fluid extraction mechanism 114 coupled to an outlet 92 formed in the chamber 82. The device 80 can also optionally include a fluid receptacle 88 disposed between the outlet 92 of the chamber 82 and the fluid extraction mechanism 114. In use, the fluid extraction mechanism 114 is effective to draw fluid into the penetrating element 110 from an outside fluid source, such as a patient's body, through the chamber 82 and the substrate 84 disposed within the chamber 82. The fluid can then be collected in the fluid receptacle 88.

The chamber 82 can have a variety of shapes and sizes, but should be adapted to retain a substrate 84, and to allow fluid to flow therethrough. As shown in FIG. 1, the chamber 82 has a generally cylindrical shape and includes a first end 106 having an inlet 90, a second end 108 having an outlet 92, and a hollow interior 91 extending therebetween and adapted to receive and hold a substrate 84. The inlet and outlet 90, 92 in the chamber 82 can each have any shape and size and, by way of non-limiting example, can be in the form of a port or a valve. Preferably, the inlet and outlet 90, 92 are each in the form of a one-way valve that is effective to control the direction of fluid flow therethrough. More preferably, the inlet 90 allows fluid to flow into the chamber 82, and the outlet 92 allows fluid to flow out of the chamber 82.

The chamber 82 can optionally include a basket (not shown) or similar structure disposed therein for holding the substrate 84. The basket, or a portion of the basket, can be permanently or removably disposed within the chamber 82, or can be integrally formed with the chamber 82. The basket, or at least a portion of the basket, is fluid permeable to allow fluid to flow through a substrate disposed therein. By way of non-limiting example, the basket can include first and second porous members, e.g., screens, positioned at a distance apart from one another and effective to hold a substrate 84 therebetween. In another embodiment, the chamber 82 can include a side-opening, slot, or door formed therein for slidably receiving the substrate 84 or basket containing a substrate. Examples of suitable chambers 82 and baskets for use with the device of the present invention are disclosed in U.S. patent application Ser. No. 10/223,674, filed on Aug. 19, 2002 and entitled "Device For Controlling Fluid Flow Through a Medium," the teachings of which are hereby incorporated by reference.

The inlet 90 in the chamber 82 is coupled to the penetrating element 110, preferably via a first conduit 100, and is effective to allow fluid to flow from the penetrating element 110 into the chamber 82. The penetrating element 110 can have a variety of configurations, and is adapted to penetrate into tissue and/or bone to allow fluid to be extracted therefrom. As shown in FIG. 1, the penetrating element 110 includes a handle 112 and an elongate tissue piercing member 86, e.g., a needle. Suitable examples of an elongate penetrating element 110 are disclosed in U.S. patent application Ser. No. 10/194,752, filed on Jul. 12, 2002, and entitled "Bone Marrow Aspirator," which is hereby incorporated by reference in its entirety.

The outlet 92 in the chamber 82 is coupled to a fluid extraction mechanism 114, preferably via a fluid receptacle 88. A second conduit 108 can extend from the outlet 92 in the chamber 82 to an inlet 94 formed in the fluid receptacle 88, and a third conduit 104 can extend from an outlet 96 in the fluid receptacle 88 to the fluid extraction mechanism 114. The fluid receptacle 88 can have virtually any shape and size, but should be effective to hold a predetermined amount of fluid extracted from a patient. The receptacle 88 should also be airtight to allow fluid to be drawn into the penetrating element 110 from an outside fluid source, through the chamber 82, and into the fluid receptacle 88. As shown in FIG. 1, the receptacle 88 includes an inlet 94 coupled to the chamber 82 via conduit 108, and an outlet 96 coupled to a fluid extraction mechanism 114 via conduit 104. The inlet and outlets 94, 96 can have any configuration, and can be formed anywhere in the receptacle 88. Preferably, however, the inlet 94 is positioned to allow fluid to drain into the receptacle 88 from the chamber 82, and the outlet 96 is positioned at a location that will prevent fluid from being pulled therethrough into conduit 104. This will allow the fluid extraction mechanism 114 to create a vacuum force within the device 80 without drawing fluid into the fluid extraction mechanism 114.

The fluid extraction mechanism 114, which is coupled to the fluid receptacle 88, or optionally directly to the outlet 92 in the chamber 82, can also have a variety of configurations.

The extraction mechanism 114 should, however, be effective to create a vacuum force in the device 80 to draw fluid into the penetrating element 110, through the chamber 82 and the substrate 84 disposed within the chamber 82, and into the fluid receptacle 88. As shown in FIG. 1, the fluid extraction mechanism 114 is in the form of a vacuum pump. A person having ordinary skill in the art will appreciate that a variety of devices can be used to extract fluid through the system 80, including both mechanical and/or electrical devices.

In use, the penetrating element 110 is positioned at a fluid site in a patient's body, or the inlet 90 in the chamber 82 is mated to an external fluid source. The fluid extraction mechanism 114 is then activated to pull fluid from the patient through the device 80, whereby fluid travels from the penetrating element 110 to the chamber 82 via conduit 100, through the substrate 84 disposed within the chamber 82, and to the fluid receptacle 88 via conduit 108. The process of extracting fluid through the device 80 can be repeated several times, as desired.

The device 80 can also optionally include fluid flow control mechanisms for controlling the rate of fluid flow through the device 80. By way of non-limiting example, the fluid extraction mechanism 114 can be adapted to pull fluid through the device 80 at a predetermined rate. Alternatively, or in addition, the conduits 100, 108, and 104 can have a size effective to control the rate of fluid flow therethrough. The inlets and outlets 90, 92, 94, 96 in the chamber 82 and/or fluid receptacle 88 can also be adapted to regulate the rate of fluid flow. A person having ordinary skill in the art will appreciate that a variety of techniques can be used to control the rate of fluid flow through the device 80.

Figure 2:
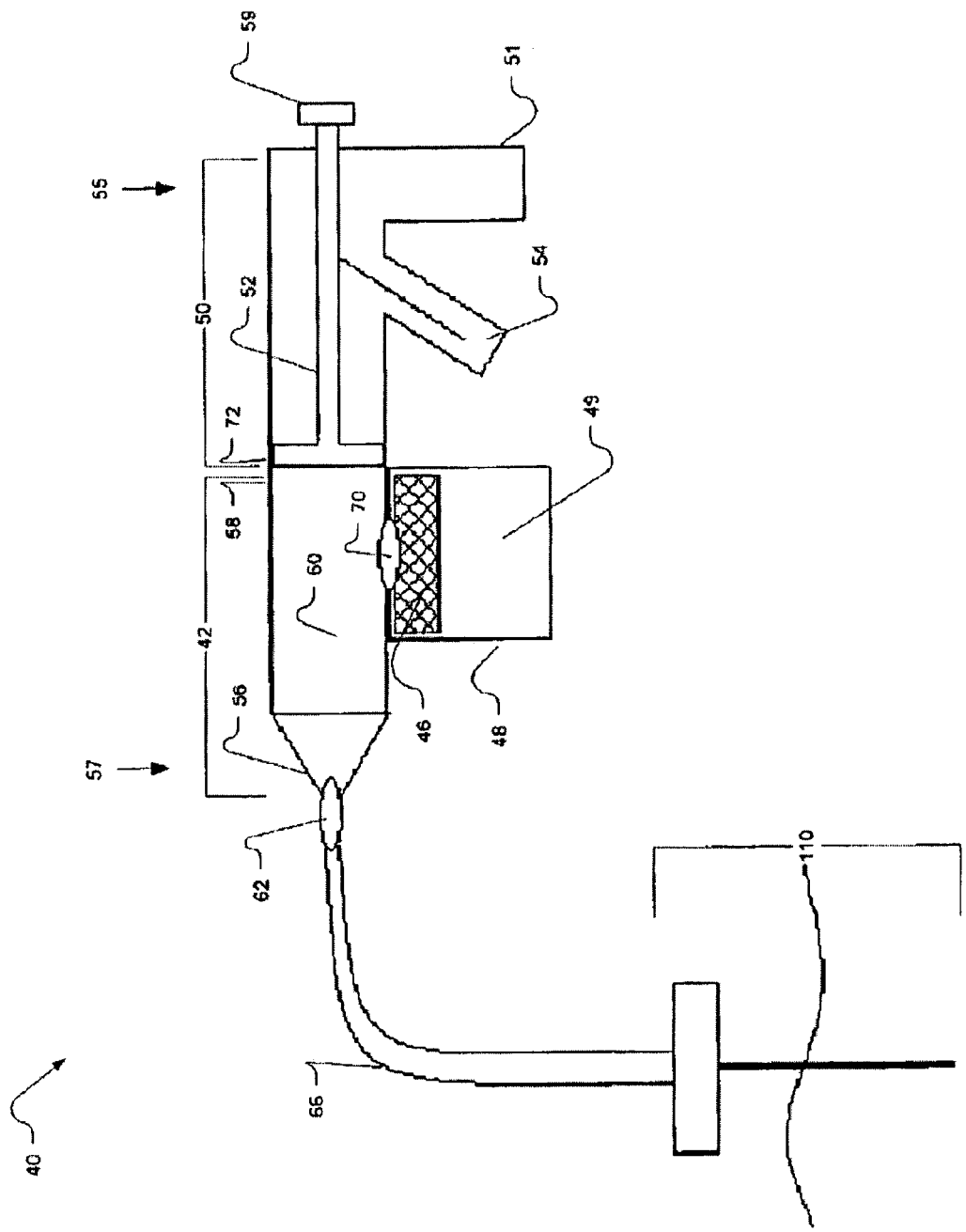
FIG. 2 is a diagram illustrating another embodiment of a bone marrow aspiration device according to the present invention in which the chamber, fluid extraction mechanism, and fluid receptacle are disposed within a housing.

FIG. 2 illustrates another embodiment of a bone marrow aspiration device 40 according to the present invention. The device 40 is similar to device 80 described with respect to FIG. 1, except that the fluid extraction mechanism 50, chamber 42, and fluid receptacle 48 are disposed within a housing 51 and combined into a single device 40 that is adapted to mate to an external fluid source, such as an elongate penetrating element 110 described about with respect to FIG. 1. As shown in FIG. 2, the device 40 generally includes a housing 51 having proximal and distal ends 55, 57, a chamber 42 formed within the distal end 57 of the housing 51, and a fluid extraction mechanism 50 disposed within the proximal end 55 of the housing 51. The device 40 can also include a fluid receptacle 48 or reservoir which forms part of the chamber 42 and is preferably integrally formed with, fixedly attached to, or removably attached to the housing 51. One of the fluid receptacle 48 and the chamber 42 is adapted to retain a substrate 46. In use, fluid is drawn into the chamber 42 from an external fluid source, such as a patient's body via the penetrating element 110, and is pushed or pulled through the substrate 46 and collected in the fluid receptacle 48.

The chamber 42 can have virtually any shape and size, but is preferably formed within a distal portion of the housing 51 and includes a proximal end 58, a distal end 56, and an inner lumen 60 extending therebetween. The proximal end 58 of the chamber 42 is adapted to slidably receive the fluid extraction mechanism, e.g., plunger 50, and the distal end 56 of the chamber 42 is adapted to mate with an external fluid source, or to a penetrating element 110. An inlet 62 is formed in the distal end 56 of the chamber 42 and is adapted to mate to the external fluid source, and an outlet 70 is formed adjacent the proximal end 58 of the chamber 42 and is coupled to the fluid receptacle 48. The inlet 62 and outlet 70 can each have a variety of configurations, but are preferably one-way valves effective to control the direction of fluid flow. In an exemplary embodiment, the inlet 62 is effective to allow fluid to flow only in a direction into the inner lumen 60 of the chamber 42, and the outlet 70 is effective to allow fluid to flow only in a direction from the inner lumen 60 of the chamber 42 into the fluid receptacle 48.

The fluid receptacle 48 can also have virtually any shape and size, and can be permanently or removably mated to the chamber 42. The fluid receptacle 48 should be adapted to hold a predetermined amount of fluid. Preferably, the fluid receptacle 48 has a generally cylindrical shape having an inner lumen 49 formed therein, and is removably attached to the housing 51 such that the inner lumen 49 of the fluid receptacle 48 is in fluid communication with the inner lumen 60 of the chamber 42 via outlet 70. The fluid receptacle 48 can be attached to the housing 51 using a variety of mating techniques, but is preferably attached to the housing 51 using a threaded engagement (not shown).

The device 40 further includes a substrate 46 disposed within the inner lumen 60 of the chamber 42, within the fluid receptacle 48, or between the chamber 42 and fluid receptacle 48. Preferably, the substrate 46 is disposed within the fluid receptacle 48 just downstream of the outlet 70, as shown in FIG. 2. The substrate 46 can be disposed within a fluid permeable basket or container, as discussed above with reference to FIG. 1, or alternatively, the fluid receptacle 48 itself can be modified to retain the substrate 46. By way of non-limiting example, the fluid receptacle 48 can include first and second porous members (not shown) positioned a distance apart from one another and effective to retain a substrate therebetween. A person having ordinary skill in the art will appreciate that a variety of techniques can be used to position a substrate within the fluid receptacle 48, or alternatively within the chamber 42.

In another embodiment (not shown), the substrate 46 can be disposed within the chamber 42, adjacent the inlet 62, thereby eliminating the need for a fluid receptacle 48 and reducing the volume of the system 40. The reduced volume will allow fluid to be drawn into the system 40 without requiring significant vacuum forces. In an exemplary embodiment, the chamber 42 and fluid receptacle 48 are adapted to retain a volume of fluid in the range of about 20 cc to 60 cc.

The fluid extraction mechanism 50, which is coupled to the proximal end 58 of the chamber 42, can also have a variety of configurations. Preferably, as shown in FIG. 2, the fluid extraction mechanism 50 is a plunger slidably disposed within the housing 51. The plunger 50 includes an elongate portion 52 having a distal, sealing member 72, such as a gasket or grommet, formed on a distal end thereof for creating a fluid-tight seal between the chamber 42 and the proximal portion of the housing 51. The plunger 50 can also include a proximal, handle member 59 extending proximally from the housing 51. The handle 59 can be used to grasp and move the plunger 50 within the housing to create a vacuum force to direct fluid through the device 40. The elongate portion 52 of the plunger 50 can optionally be mated to a trigger mechanism 54 which is effective to engage and move the plunger 50 in one of a proximal direction or a distal direction. Preferably, the trigger mechanism 54 is used to move the plunger 50 in a proximal direction to create a vacuum force to draw fluid into the chamber 42, and the handle 59 is used to move the plunger 50 in a distal direction to push fluid through outlet 70 and into the receptacle 48, wherein the fluid passes through the substrate 46. The trigger mechanism 54 can also be adapted to move the plunger 50 in predetermined increments. In an exemplary embodiment, the trigger mechanism 54 is adapted to draw about 2 cc of fluid into the chamber 42. This is particularly effective to allow 2 cc samples of fluid to be drawn from several fluid sites within a patient's body. By way of non-limiting example, the trigger mechanism 54 can be a ratchet-type mechanism. A person having ordinary skill in the art will appreciate that a variety of techniques can be used for moving the plunger 50 within the housing 51.

In use, the inlet 62 formed in the distal end 57 of the housing 51 is coupled to an external fluid source, such as an elongate penetrating element 110 via a conduit 66. A substrate 46 is positioned within the fluid receptacle 48, which is mated to the housing 51 and in fluid communication with the chamber 42 via outlet 70. The trigger mechanism 54 is then grasped and actuated to create a vacuum within the chamber 42, thereby drawing fluid through the elongate penetrating element 44 and into the inner lumen 60 of the chamber 42. The one-way valve 70 prevents fluid from being drawn into the chamber 42 from the receptacle 48. The fluid can then optionally flow freely into the fluid receptacle 48 via outlet 70, or the handle 59 can be grasped to move the plunger 50 distally, thereby forcing fluid into the receptacle 48 and through the substrate 46. The one-way valve 62 prevents fluid from flowing back out of the chamber 42 and into conduit 66. The process can be repeated several times as desired.

Figure 3:
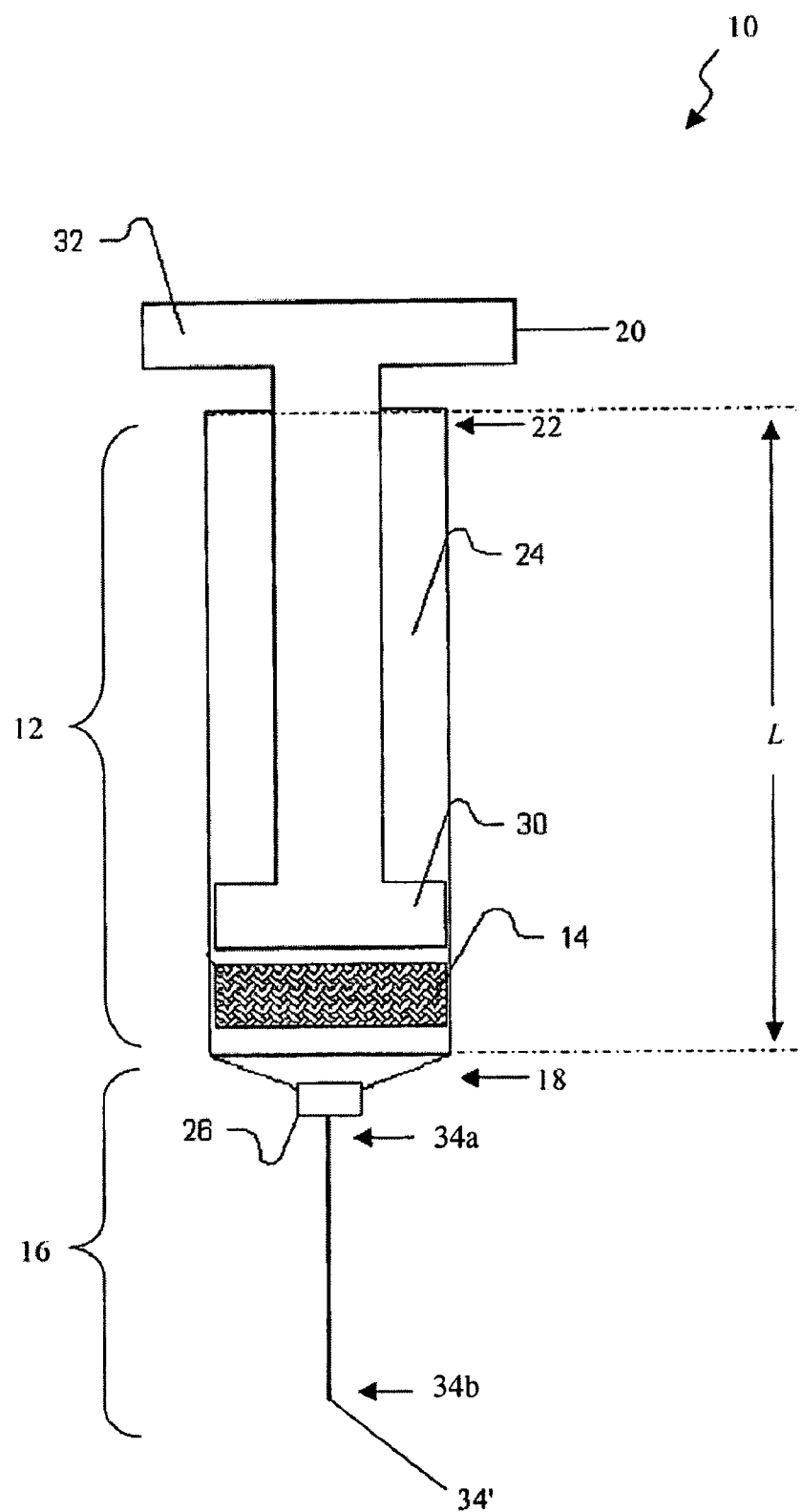
FIG. 3 is a diagram illustrating another embodiment of a bone marrow aspiration device having a chamber, an elongate penetrating element extending from a distal end of the chamber, and fluid extraction mechanism disposed within the chamber.

FIG. 3 illustrates yet another embodiment of a bone marrow aspiration device 10 according to the present invention. In this embodiment, the chamber 12, fluid extraction mechanism 20, and elongate penetrating element 16 are combined to form an all-in-one device 10. As shown, the device 10 generally includes a chamber 12 adapted to retain a substrate 14, an elongate penetrating element 16 coupled to a distal end 18 of the chamber 12, and a fluid extraction mechanism 20 slidably disposed within a proximal end 22 of the chamber 12. The fluid extraction mechanism 20 is effective to draw fluid from a patient or other outside fluid source, through the penetrating element 16, into the chamber 12, and through the substrate 14.

The chamber 12 can have a variety of shapes and sizes, but is preferably an elongate cylindrical member having a proximal end 22, a distal end 18, and an inner lumen 24 extending therebetween. As shown in FIG. 3, the chamber 12 is in the form of a syringe barrel and includes a tapered distal end 18 adapted to mate to a penetrating element 16, and an open proximal end 22 adapted to slidably receive the fluid extraction mechanism 20. The proximal end 22 of the chamber 12 can optionally include a flange (not shown) or similar feature formed around an outer surface of the proximal end 22 to facilitate ease of handling. The inner lumen 24 of the chamber 12 should have a size sufficient to allow slidable movement of the fluid extraction mechanism 20 therein, and to retain a predetermined amount of fluid. Preferably, the inner lumen 24 has a length L that is sufficient to allow the fluid extraction mechanism 20 to be moved between the proximal and distal ends 22, 18 to draw a predetermined amount of fluid into the chamber 12. Moreover, the length L should be sufficient to enable the fluid extraction mechanism 20 to be moved without coming into contact with the substrate 14.

The chamber 12 is adapted to retain a substrate 14, which can be positioned anywhere within the chamber 12, but is preferably positioned in the distal portion of the chamber 12. In one embodiment, the chamber 12 can include a basket or tray (not shown) formed therein for receiving the substrate 14. The basket or tray can be formed from first and second porous members, e.g., screens, positioned a distance apart from one another and effective to retain a substrate 14 therebetween. The porous members can be mated to one another, and can be removably or permanently disposed within the chamber. Alternatively, or in addition, the chamber 12 can include a side opening or door (not shown) formed therein for allowing the substrate 14, or a container holding a substrate 14, to be inserted and withdrawn from the chamber 12. As previously stated, examples of suitable containers 28 for use with the device of the present invention are disclosed in U.S. patent application Ser. No. 10/223,674, filed on Aug. 19, 2002 and entitled "Devices For Controlling Fluid Flow Through A Medium," the teachings of which are hereby incorporated by reference. A person having ordinary skill in the art will appreciate that a variety of techniques can be used to retain a substrate within the chamber 12.

The elongate penetrating element 16 can also have a variety of shapes and sizes, but is preferably an elongate, cylindrical member having a proximal end 34a, a distal end 34b and an inner lumen (not shown) extending therebetween. The distal end 34b should be adapted to penetrate into tissue and/or bone, and thus preferably includes a distalmost piercing tip 34' in fluid communication with the inner lumen. In an exemplary embodiment, the elongate penetrating element 16 is a needle that is removably mated to the distal end 18 of the chamber 12. The elongate penetrating element 16 can be mated to the distal end 18 of the chamber 12 using a variety of mating techniques. FIG. 3 illustrates one embodiment of a mating element in the form of a standard luer 26. The luer 26 includes an inner lumen having threads formed therein for mating to corresponding threads formed on each of the distal end 18 of the chamber 12 and the proximal end 34a of the penetrating element 16. The luer 26 can alternatively be permanently mated to the penetrating element 16 to allow removal of both the luer 26 and the penetrating element 16 from the chamber 12. A person having ordinary skill in the art will appreciate that a variety of engagement techniques can be used to mate the penetrating element 16 to the chamber 12, including, for example, a snap fit engagement, an interference fit, and a magnetic engagement. Those skilled in the art will appreciate that various techniques can be used for permanently or releasably mating the penetrating element 16 to the chamber 12.

While an elongate penetrating element 16 is shown, the distal end 18 of the chamber 12 can be adapted to mate to any device or external fluid source. For example, the elongate penetrating element 16 can be replaced with a flexible tube that can mate to a separate penetrating device, such as a needle, or to a fluid source.

Still referring to FIG. 3, the fluid extraction mechanism 20, which is slidably disposed within the proximal end 22 of the chamber 12, is effective to withdraw fluid from a patient or other reservoir into the chamber 12 and through the substrate 14 disposed within the chamber. The fluid extraction mechanism 20 can have virtually any configuration, but is preferably a plunger having a proximal end 32 and a distal end 30. The proximal end 32, e.g., handle, preferably has a shape adapted to facilitating grasping thereof to allow a user to move the fluid extraction mechanism 20 with respect to the chamber 12. The distal end 30 of the fluid extraction mechanism 20 is slidably disposed within the inner lumen 24 of the chamber 12, and has a size and shape adapted to form a seal within the chamber 12 to create a vacuum force. The distal end 30 can optionally include a sealing member, such as a gasket or grommet, to assist in maintaining a fluid-tight seal within the chamber 12. The sealing member should, however, allow slidable movement of the fluid extraction mechanism 20 with respect to the chamber 12.

In use, the extraction mechanism 20 is movable between a first position (shown in FIG. 3), in which the fluid extraction mechanism 20 is substantially disposed within the chamber 12, and a second position (not shown), in which the fluid extraction mechanism 20 is substantially extended from the chamber 12. Movement of the fluid extraction mechanism 20 from the first position to the second position creates a vacuum force within the chamber 12 that is effective to draw fluid from the external fluid source, e.g., the patient, via the penetrating element 16 into the chamber 12. Conversely, movement from the second position to the first position will create a pressure in the chamber 12, thereby causing fluid disposed within the chamber 12 to be pushed out of the chamber through the penetrating element 16, or more preferably, through an outlet port formed in the chamber 12.

Movement of the fluid extraction mechanism 20 can be effected manually and/or mechanically. By way of non-limiting example, the fluid extraction mechanism 20 can be mated to a ratchet-style handle or similar mechanism for moving the plunger 20. A person having ordinary skill in the art will appreciate that virtually any actuation mechanism can be employed with the devices according to the present invention. Moreover, while a plunger 20 is shown for creating a vacuum force within the chamber 12, a variety of other fluid extraction mechanisms can be used. For example, the chamber 12 can be coupled to a vacuum pump, as discussed with respect to FIG. 2.

The device 10 can also optionally include a mechanism for controlling the rate of fluid flow through the chamber 12 and the substrate 14. By way of non-limiting example, the penetrating element 16 can include an inner lumen having a diameter that is adapted to restrict the flow of fluid therethrough. In another embodiment, the device can include micro-bore tubing disposed within the fluid flow path and having an internal lumen sized to restrict the rate of fluid flow. The micro-bore tubing is preferably disposed between the penetrating element 16 and the chamber 12, for example, within the luer 26. One skilled in the art will appreciate that a variety of fluid flow control devices can be used with the present invention.

The direction of fluid flow through the device can also be controlled. By way of non-limiting example, one or more one-way or dual-check valves can be provided for controlling the direction of fluid flow. Preferably, the luer 26 is a one-way valve that allows fluid to flow only in a direction from the elongate penetrating element 16 into the chamber 12.

Figure 4:
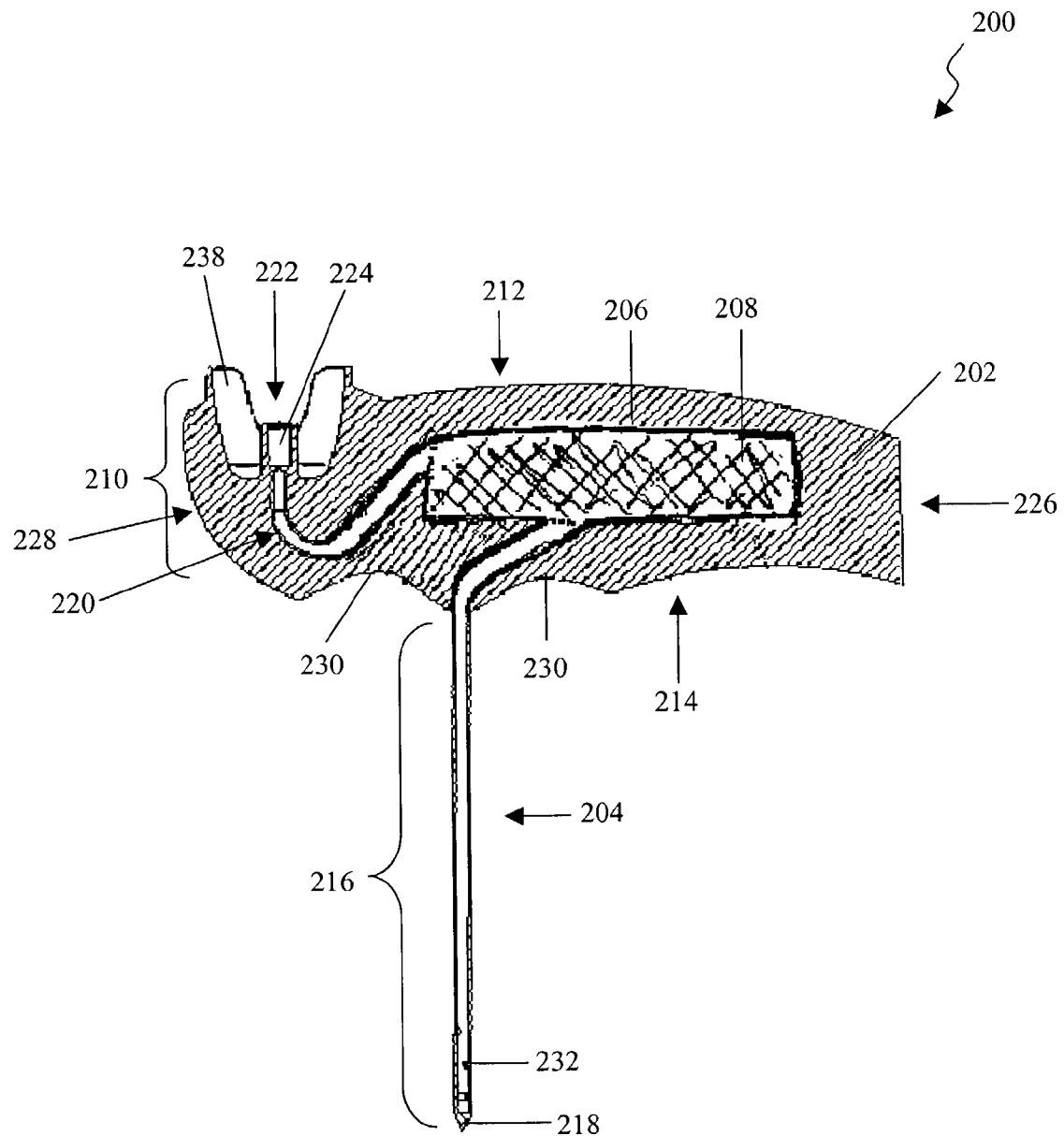
FIG. 4 is a diagram illustrating yet another embodiment of a bone marrow aspiration device having a substrate disposed within a handle of an elongate penetrating element.

FIG. 4 illustrates yet another embodiment of an aspiration device 200 having a handle 202 and an elongate penetrating element 204 coupled to the handle 202. A person having ordinary skill in the art will appreciate that the device 200 can have a variety of configurations, as generally described in U.S. patent application Ser. No. 10/194,752, entitled "Bone Marrow Aspirator," filed on Jul. 12, 2002, which is hereby incorporated by reference in its entirety.

Preferably, as shown, the handle 202 includes proximal and distal surfaces 212, 214, and first and second side surfaces 226, 228 extending between the proximal and distal surfaces 212, 214. The shape of the handle 202 is preferably adapted to facilitate single-handed use and manipulation thereof. For example, the distal surface 214 of the handle 202 can include one or more finger-receiving recesses 230. The elongate penetrating element 204 includes a proximal portion 210 coupled to the handle 202 and having a proximal end with an inlet port 224 formed therein, and a distal portion 216 having a smooth outer surface and a solid, distal piercing tip 218. A substantially cylindrical sidewall 220 defines an inner lumen 222 in the elongate penetrating element 204 which extends from the inlet port 224 to a position proximal to the distal piercing tip 218. The elongate penetrating element 204 also includes at least one opening 232 formed in the sidewall and in communication with the inner lumen. The opening 232 is preferably positioned proximal to the distal piercing tip 218.

The device 200 further includes a chamber 206 disposed within the handle 202 and adapted to retain a substrate 208. The chamber 206 is in fluid communication with the elongate penetrating element 204, and is preferably position between the proximal and distal portions 210, 216 of the penetrating element 204. The handle 202 can include a side opening or door (not shown) formed therein for providing access to the chamber 206, and the substrate 208, or container holding the substrate 208, disposed within the chamber 206.

The proximal surface 212 of the handle 202 is preferably adapted to allow access to the inlet port 224 of the elongate penetrating element 204. By way of non-limiting example, the handle 202 can include a receiving well 238 formed in or mated to the proximal surface 212 of the handle 202 and adapted to seat the base of a medical device, such as a surgical syringe, to enable mating between the medical device and the inlet port 224 on the elongate penetrating element 204. In an exemplary embodiment, as shown, the receiving well 238 has a cylindrical shape which conforms to the shape of the base of a surgical syringe. The receiving well 238 is preferably tapered along the inner surface toward the distal end to provide an interference fit with the base of a surgical syringe, and at least a portion of the receiving well 238 can extend outward from the proximal surface 212 of the handle 202. The receiving well 238 can optionally include a mating element (not shown) for mating with the surgical syringe, or other medical device. While a variety of mating techniques can be used, the receiving well 238 preferably includes threads (not shown) formed on the inner surface thereof. Other suitable mating techniques include, for example, an interference fit and a positive interlock engagement.

In use, the handle 202 is grasped and manipulated to position the elongate penetrating element 204 at a fluid site in a patient's body. A syringe or other fluid extraction mechanism is then coupled to the inlet port 224 in the elongate penetrating element 204, and activated to draw fluid up through the distal portion 216 of the penetrating element 204, through the substrate 208 disposed within the chamber 206, and through the proximal portion 210 of the penetrating element 204 where the fluid is drawn into the syringe or other fluid extraction mechanism.

It will be understood that the foregoing is only illustrative of the principles of the invention, and that various modifications can be made by those skilled in the art without departing from the scope and spirit of the invention. These three embodiments are but of few of those possible, all of which provide a bone aspiration device capable of infusing a fluid through a substrate.

What is claimed is:

1. A bone marrow aspiration device, comprising:
an elongate penetrating element having a proximal end, a distal end, and an inner lumen extending therebetween;
a chamber in communication with the proximal end of the elongate penetrating element;

a container removably disposed within the chamber and having an implantable substrate disposed therein, the container being effective to allow fluid to flow therethrough; and a fluid extraction mechanism in communication with the chamber, the fluid extraction mechanism being effective to pull fluid through the elongate penetrating element into the chamber and through the substrate.

2. The device of claim 1, wherein the chamber includes an opening sized to slidably receive the container.

3. The device of claim 1, further comprising a unidirectional valve disposed between the elongate penetrating element and the chamber, the unidirectional valve being effective to allow fluid to flow only in a direction from the elongate penetrating element to the chamber.

4. The device of claim 1, further comprising a control member mated to the fluid extraction mechanism and effective to control the amount of fluid being extracted by the fluid extraction mechanism.

5. The device of claim 4, wherein the control member is effective to control the rate of fluid being extracted by the fluid extraction mechanism.

6. The device of claim 4, wherein the control member comprises a trigger mechanism effective to actuate the fluid extraction mechanism to extract a predetermined amount of fluid.

7. The device of claim 6, wherein the trigger mechanism is effective to actuate the fluid extraction mechanism to extract a volume of fluid in the range of about 20 cc to 60 cc.

8. The device of claim 1, wherein the elongate penetrating element is removably mated to a distal end of the chamber.

9. The device of claim 1, wherein the chamber includes a proximal end in communication with the fluid extraction mechanism, and a distal end having an inlet port in communication with the proximal end of the elongate penetrating element.

10. The device of claim 9, wherein the chamber is adapted to retain the container in a position proximal to the inlet port in the chamber.

11. The device of claim 10, wherein the inlet port comprises a unidirectional valve configured to allow fluid to flow only in a direction from the elongate penetrating element into the chamber.

12. The device of claim 10, wherein the chamber comprises an elongate, cylindrical barrel, and the fluid extraction mechanism comprises a plunger disposed within the barrel and having a handle adapted to move the plunger proximally to extract fluid through the device.

13. The device of claim 12, wherein the plunger is adapted to move proximally in predetermined increments to control the amount of fluid being extracted through the device.

14. The device of claim 12, wherein the container is disc-shaped and it is adapted to be removably disposed within the cylindrical barrel of the chamber.

15. The device of claim 10, wherein the proximal end of the elongate penetrating element is removably mated to the inlet port of the chamber.

16. The device of claim 15, further comprising a standard luer connection for removably mating the proximal end of the elongate penetrating element to the inlet port of the chamber.

17. The device of claim 9, further comprising a fluid receptacle in communication with the chamber, the fluid receptacle being adapted to receive fluid passed through the chamber and through the substrate disposed within the container in the chamber.

18. The device of claim 17, wherein the container is disposed at an inlet port of the fluid receptacle.

19. The device of claim 18, wherein the fluid receptacle is removably mated to the chamber.

20. The device of claim 17, further comprising a unidirectional valve disposed between the chamber and the fluid receptacle, the unidirectional valve being effective to allow fluid to flow only in the direction from the chamber to the fluid receptacle.

21. The device of claim 20, wherein the unidirectional valve is disposed at the proximal end of the chamber such that fluid can flow from the chamber through the unidirectional valve, then through the substrate in the container, and into the fluid receptacle.

22. The device of claim 9, further comprising a conduit extending between the proximal end of the elongate penetrating element and the inlet port of the chamber such that fluid can flow from the elongate penetrating element, through the conduit, and into the chamber.

23. The device of claim 17, wherein a conduit is removably attached to the proximal end of the elongate penetrating element and an inlet port in the chamber.

24. The device of claim 1, further comprising a fluid receptacle disposed between the chamber and the fluid extraction mechanism.

25. The device of claim 24, wherein the chamber includes an inlet port in fluid communication with the proximal end of the elongate penetrating element, and an outlet port in communication with the fluid receptacle, and wherein the fluid receptacle includes an inlet port in communication with the outlet port of the chamber, and an outlet port in communication with the fluid extraction mechanism.

26. The device of claim 25, further comprising:

a first conduit extending between the proximal end of the elongate penetrating element and the inlet port of the chamber, the first conduit being effective to allow fluid to flow from the elongate penetrating element to the chamber;

a second conduit extending from the outlet port of the chamber to an inlet port in the fluid receptacle, the second conduit being effective to allow fluid to flow from the chamber to the receptacle; and a third conduit extending from the outlet port of the fluid receptacle to the fluid extraction mechanism.

27. The device of claim 26, wherein the fluid extraction mechanism comprises a suction element effective to extract fluid from the elongate penetrating element, through the chamber, and into the fluid receptacle.

28. The device of claim 27, wherein the suction element comprises a vacuum pump.

29. The device of claim 26, further comprising a unidirectional valve disposed at the inlet port of the fluid receptacle, the unidirectional valve being effective to enable fluid to flow into the inlet port of the fluid receptacle, and the prevent fluid from flow out of the inlet port of the fluid receptacle.

30. A method for preparing an implantable substrate, comprising:

providing a bone marrow aspirator device having an elongate penetrating element having a proximal end, a distal end adapted to penetrate bone, and an inner lumen extending therebetween, a chamber in fluid communication with the proximal end of the elongate penetrating element, a container disposed within the chamber and adapted to allow fluid to flow therethrough;

an implantable substrate disposed within the chamber, and a fluid extraction mechanism effective to pull fluid through the elongate penetrating element, into the chamber, and through the substrate;

penetrating the distal end of the elongate penetrating element into a patient;

actuating the fluid extraction mechanism to pull fluid from the patient through the elongate penetrating element, into the chamber, and through the substrate, thereby concentrating cells from a biological material within the substrate.

31. The method of claim 30, wherein the elongate penetrating element is penetrated into a patient's bone and the fluid being extracted is bone marrow.

32. The method of claim 31, further comprising wherein the substrate present in the container, the substrate being is selected from the group consisting of allograft bone, autograft bone, synthetic materials, purified materials, and combinations thereof.

33. The method of claim 31, wherein the chamber comprises an elongate, cylindrical barrel having a distal end removably mated to the proximal end of the elongate penetrating element, and the fluid extraction mechanism comprises a plunger disposed within the barrel and having a handle adapted to move the plunger proximally to extract fluid through the device.

* * * * *